US 6,660,746 B1
United States Patent
Schindler et al.

(10) Patent No.: US 6,660,746 B1
(45) Date of Patent: Dec. 9, 2003

(54) SUBSTITUTED 4-AMINO-2-ARYL-TETRAHYDOQUINAZOLINES, THEIR PREPARATION, THEIR USE AND PHARMACEUTICAL PREPARATIONS COMPRISING THEM

(75) Inventors: Ursula Schindler, Bad Soden (DE); Karl Schönafinger, Alzenau (DE); Hartmut Strobel, Liederbach (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/497,723

(22) Filed: Feb. 4, 2000

(30) Foreign Application Priority Data

Feb. 5, 1999 (DE) .......................... 199 04 710

(51) Int. Cl.$^7$ ................... A61K 31/517; C07D 239/72; C07D 239/94
(52) U.S. Cl. ................ 514/266.1; 514/258.1; 514/266.4; 544/283; 544/242; 544/293
(58) Field of Search .................... 514/258.1, 266.1, 514/266.4; 544/283, 242, 293

(56) References Cited

U.S. PATENT DOCUMENTS

| | | | |
|---|---|---|---|
| 3,322,759 A | 5/1967 | Carney et al. | 260/247.5 |
| 3,346,452 A | 10/1967 | Carney et al. | 167/65 |
| 4,610,984 A * | 9/1986 | Schindler et al. | 514/235 |
| 6,245,760 B1 * | 6/2001 | Wei He et al. | 514/234.8 |

FOREIGN PATENT DOCUMENTS

| | | | |
|---|---|---|---|
| EP | 407899 | * | 1/1991 |
| EP | 0 667 345 A1 | | 8/1995 |
| EP | 407899 | * | 10/1996 |
| EP | 0 826 673 A1 | | 3/1998 |
| JP | 10130150 | * | 5/1998 |
| WO | 9632383 | * | 10/1996 |
| WO | WO 97/47601 | | 12/1997 |
| WO | WO 98/16223 | | 4/1998 |
| WO | WO 00/09496 | | 2/2000 |
| WO | WO 00/31047 | | 6/2000 |

OTHER PUBLICATIONS

CAS Abstr. :Honda et al, 111:6684–1989:406684, also cited as;Fukui Dai. Kogakubu Kenkyu Hokoku,36/2, 1655–81(1988).*
Liddendirff et al;"Multiple roles of the messenger Molecule cGMP in testicular function"; Andrologia,32/1, 55–9(2000).*
Honda, Itaru et al.,"Synth . . . of triazines";Fukui Daigaku . . . Hokoku 36/2. 165–81(Feb. 1988.*
Abstract: JP 07 228573 A—Masahiro Kataoka, Katsuhiko Hino, and Yoshiaki Ochi, "Preparation of 2–phenylcycloalkanopyrimidine derivatives as antagonists of serotonin 8, receptor," *Chemical Abstracts*, Columbus, Ohio, vol. 124, 87634q, 1996.

Abstract: JP 10 130150 A—Akiya Murata, Katsuhiko Hino, Kiyoshi Furukawa, Makoto Oka, and Mari Ito, "Preparation of acetic acid amide derivatives as drugs," *Chemical Abstracts*, Columbus, Ohio, vol. 129, 54385e, 1998.
International Search Report mailed May 29, 2000.
Abstract: 07–228573—Yoshiaki Ochi, "2–Phenylcycloalkkanopyrimidine Derivative," European Patent Office Abstract.
Louis J. Ignarro, "Regulation of Cytosolic Guanylyl Cyclase by Porphyrins and Metalloporphrins," *Advances in Pharmacology*, vol. 26: 35–65 (1994).
Feng–Nien Ko, Chin–Chung Wu, Sheng–Chu Kuo, Fang–Yu Lee, and Che–Ming Teng, "YC–1, a Novel Activator of Platelet Guanylate Cyclase," *Blood*, vol. 84 (12), 4226–4233 (Dec. 15, 1994).
Douglas J. Pettibone, Charles S. Sweet, Edwin A. Risley and Thomas Kennedy, "A Structurally Novel Stimulator of Guanylate Cyclase with Long–Lasting Hypotensive Activity in the Dog," *European Journal of Pharmacology*, vol. 116: 307–312 (1985).
D. L. Vesely, "B complex vitamins activate rat guanylate cyclase and increase cyclic GMP levels," *European Journal of Clinical Investigation*, vol. 15: 258–262 (1985).

(List continued on next page.)

*Primary Examiner*—Mukund J. Shah
*Assistant Examiner*—Sudhaker B. Patel
(74) *Attorney, Agent, or Firm*—Finnegan, Henderson, Farabow, Garrett & Dunner, LLP

(57) ABSTRACT

The present invention relates to compounds of formula I:

wherein $R^1$, $R^2$, and $R^3$ have the meanings indicated in the specification, which are valuable pharmaceutical active compounds for the therapy and prophylaxis of diseases such as cardiovascular disorders such as high blood pressure, angina pectoris, cardiac insufficiency, thromboses, or atherosclerosis. Compounds of formula I have the ability to modulate the endogenous production of cyclic guanosine monophosphate (cGMP) and are generally suitable for the therapy and prophylaxis of disease states which are associated with a disturbed cGMP balance. The invention furthermore relates to processes for the preparation of compounds formula I, methods of therapy and prophylaxis of the designated disease states and for the production of pharmaceuticals therefor, and pharmaceutical compositions which comprise at least one compound of formula I.

13 Claims, No Drawings

OTHER PUBLICATIONS

Chin–Chung Wu, Feng–Nien Ko, Sheng–Chu Kuo, Fang–Yu Lee, and Che–Ming Teng, "YC–1 inhibited human platelet aggregation through NO–independent activation of solube guanylate cyclase," *British Journal of Pharmacology*, vol. 116: 1973–1978 (1995).

Sheu–Meei Yu and Sheng–Chu Kuo, "Vasorelaxant effect of isoliquiritigenin, a novel soluble guanylate cyclase activator, in rat aorta," *British Journal of Pharmacology*, vol. 114: 1587–1594 (1995).

Sheu M. Yu, Zhi J. Chen, Jih H. Guh, Fang Y. Lee, and Sheng C. Kuo, "Mechanism of anti–proliferation caused by YC–1, an indazole derivative, in cultured rat A 10 vascular smooth–muscle cells," *Biochem. J.*, vol. 306: 787–792 (1995).

* cited by examiner

SUBSTITUTED 4-AMINO-2-ARYL-TETRAHYDOQUINAZOLINES, THEIR PREPARATION, THEIR USE AND PHARMACEUTICAL PREPARATIONS COMPRISING THEM

The present invention relates to compounds of formula I

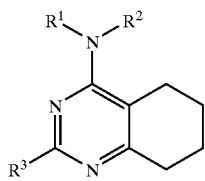

wherein $R^1$, $R^2$ and $R^3$ have the meanings indicated below, which are valuable pharmaceutically active compounds for the therapy and prophylaxis of diseases, for example, of cardiovascular disorders such as high blood pressure, angina pectoris, cardiac insufficiency, thromboses, or atherosclerosis. The compounds of formula I have the ability to modulate the endogenous production of cyclic guanosine monophosphate (cGMP) and are generally suitable for the therapy and prophylaxis of disease states which are associated with a disturbed cGMP balance. The invention furthermore relates to processes for the preparation of compounds of formula I, their use for therapy and prophylaxis of the designated disease states, and for the production of pharmaceuticals therefor, and pharmaceutical compositions which comprise a compound of formula I.

cGMP is an important intracellular messenger which triggers a number of pharmacological effects by means of the modulation of cGMP-dependent protein kinases, phosphodiesterases, and ion channels. Examples are smooth muscle relaxation, the inhibition of platelet activation, and the inhibition of smooth muscle cell proliferation and leukocyte adhesion. cGMP is produced by particulate and soluble guanylate cyclases as a response to a number of extracellular and intracellular stimuli. In the case of particulate guanylate cyclases, the stimulation essentially takes place by means of peptide signal substances, such as the atrial natriuretic peptide or the cerebral natriuretic peptide. The soluble guanylate cyclases (sGC), which are cytosolic, heterodimeric heme proteins, however, are essentially regulated by a family of low molecular weight, enzymatically formed factors. The most important stimulant is nitrogen monoxide (NO) or a closely related species. The importance of other factors such as carbon monoxide or the hydroxyl radical is still largely unclear. The binding of NO to the heme with formation of a pentacoordinated heme-nitrosyl complex has been discussed as a mechanism of activation by NO. The release associated therewith of the histidine which is bound to the iron in the basal state converts the enzyme into the activated conformation.

Active soluble guanylate cyclases are each composed of an α- and a β-subunit. Several subtypes of the subunits are described which differ from one another with respect to sequence, tissue-specific distribution, and expression in various stages of development. Subtypes $\alpha_1$ and $\beta_1$ are mainly expressed in the brain and the lung, while β2 is especially found in liver and kidney. Subtype $\alpha_2$ was detected in human fetal brain. Subunits designated as $\alpha_3$ and $\beta_3$ were isolated from human brain and are homologous to $\alpha_1$ and $\beta_1$. More recent studies point to an $\alpha_{2i}$ subunit, which contains an insert in the catalytic domain. All subunits show great homology in the region of the catalytic domain. The enzymes probably contain one heme per heterodimer, which is bonded via $\beta_1$-Cys-78 and/or $\beta_1$-His-105 and is part of the regulatory center.

The formation of guanylate cyclase-activating factors can be decreased under pathological conditions, or increased degradation thereof can take place, for example, as a result of the increased occurrence of free radicals. The decreased activation of the sGC resulting therefrom leads, via the attenuation of the respective cGMP-mediated cell response, to an increase in the blood pressure, to platelet activation, or to increased cell proliferation or adhesion, for example. As a result, the formation of endothelial dysfunction, atherosclerosis, hypertension, stable or unstable angina pectoris, thromboses, myocardial infarcts, strokes, or erectile dysfunction occurs. The pharmacological stimulation of the sGC offers a possibility for the normalization of cGMP production and thus allows the treatment and prevention of such diseases.

For the pharmacological stimulation of sGC until now, almost exclusively compounds were used whose action is based on an intermediate release of NO, for example, organic nitrates. The disadvantage of this method of treatment lies in the development of tolerance and weakening of action and the higher dose which therefore becomes necessary.

Various sGC stimulators which do not act via a release of NO were described by Vesely in a series of publications. However, the compounds described, which are mostly hormones, plant hormones, vitamins, or natural substances such as lizard toxins, predominantly showed only weak effects on cGMP formation in cell lysates (D. L. Vesely, *Eur. J. Clin. Invest.* 15 (1985) 258; D. L. Vesely, *Biochem. Biophys. Res. Comm.* 88 (1979) 1244). Stimulation of heme-free guanylate cyclase by protoporphyrin IX was detected by Ignarro et al. (*Adv. Pharmacol.* 26 (1994) 35). Pettibone et al. (*Eur. J. Pharmacol.* 116 (1985) 307) described a hypotensive action for diphenyliodonium hexafluorophoshate and attributed this to a stimulation of sGC. Isoliquiritiginin, which shows a relaxant action on isolated rat aortas, likewise activates sGC according to Yu et al. (*Brit. J. Pharmacol.* 114 (1995) 1587). Ko et al. (*Blood* 84 (1994) 4226), Yu et al. (*Biochem. J.* 306 (1995) 787) and Wu et al. (*Brt. J. Pharmacol.* 116 (1995) 1973) detected an sGC stimulating activity of 1-benzyl-3-(5-hydroxymethyl-2-furyl)indazole and demonstrated an antiproliferative and platelet-inhibiting activity. An inhibitory action on platelet aggregation for various indazoles is described in EP-A-667 345. Heterocyclylmethyl-substituted and benzyl-substituted pyrazoles exhibiting sGC stimulating activity are furthermore described in WO-A-98/16 507 and WO-A-98/16 223. Certain tetrahydroquinazolines are already known. For example, in DE-A40 29 654, 2-phenyltetrahydroquinazolines having fungicidal activity are described which in the 4-position carry specific amino substituents containing alkynyl groups. In U.S. Pat. No. 3,346,452 and U.S. Pat. No. 3,322,759, tetrahydroquinazolines are described which carry an aminoalkylamino group in the 4-position and which have analgesic activity Specific bicyclic pyrimidines are described in WO-A-97/47 601 which act as dopamine receptor antagonists and can be employed for the treatment of schizophrenia, and which carry a heterocyclylalkylamino substituent in which the heterocycle is bonded via a ring nitrogen atom. 2-Phenyl-cycloalkanopyrimidines are described in JP-A-071228 573 which are serotonin receptor antagonists and are suitable as psychopharmaceuticals, and which carry a piperazino or homopiperazino substituent in the 4-position.

2-Phenylcycloalkanopyrimidines are described in EP-A-826 673 which act on benzodiazepine receptors and have, for example, an anxiolytic activity, and which carry specific amino substituents in the 4-position which contain aminocarbonyl groups.

Surprisingly, it has now been found that the fused pyrimidines of formula I according to the invention bring about strong guanylate cyclase activation, which makes them suitable for the therapy and prophylaxis of diseases which are associated with a low cGMP level.

The present invention thus relates to compounds of formula I

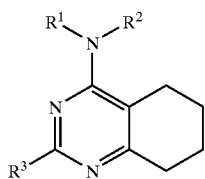

I wherein $R^1$ and $R^2$, which are selected independently of one another and which can be identical or different, are hydrogen, or $(C_1-C_{10})$-alkyl which can be substituted by one or more identical or different substituents selected from hydroxy, $(C_1-C_4)$-alkoxy, $(C_1-C_4)$-alkyl-$S(O)_m$—, $(C_3-C_7)$-cycloalkyl, phenyl, naphthyl, and pyridyl, or are $(C_3-C_9)$-cycloalkyl which can be substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-$SO_2$—NH—, and phenyl-$SO_2$—NH—, or are a residue of a 5-membered to 7-membered saturated heterocyclic ring which contains one or two identical or different heteroatom ring members selected from O, $NR^{10}$, and $S(O)_m$ and which can be substituted by one or more identical or different substituents selected from $(C_1-C_4)$-alkyl, hydroxy, and aryl-$(C_1-C_4)$-alkyl-, with the exception that $R^1$ and $R^2$ cannot simultaneously be hydrogen, or the residue $R^1R^2N$— is a residue of a 5-membered to 7-membered saturated heterocyclic ring bonded via a ring nitrogen atom which in addition to the nitrogen atom bonded to the tetrahydroquinazoline ring can contain one further heteroatom ring member selected from O and $S(O)_m$ and which can be substituted by one or more identical or different substituents selected from $(C_1-C_4)$-alkyl, phenyl, hydroxy, $(C_1-C_4)$-alkoxy, hydroxy-$(C_1-C_4)$-alkyl-, and $R^{11}R^{12}N$—, where phenyl groups, naphthyl groups, pyridyl groups and benzyl groups present in $R^1$, $R^2$ and $R^1R^2N$— can be unsubstituted or substituted on the aromatic ring by one or more identical or different substituents selected from halogen, $(C_1-C_4)$-alkyl, phenyl, $CF_3$, $NO_2$, OH, —O—$(C_1-C_4)$-alkyl, —O—$(C_2-C_4)$-alkyl-$(C_1-C_4)$-alkyl, $(C_1-C_2)$-alkylenedioxy, $NH_2$, —NH—$(C_1-C_4)$-alkyl, —N—$((C_1-C_4)$-alkyl$)_2$, —NH—CHO, —NH—CO—$(C_1-C_4)$-alkyl, CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO, and —CO—$(C_1-C_4)$-alkyl;

$R^3$ is aryl as defined below, but cannot be unsubstituted phenyl;

$R^{10}$ is hydrogen, $(C_1-C_4)$-alkyl, aryl-$(C_1-C_4)$-alkyl-, hydroxy-$(C_1-C_4)$-alkyl-, hydroxycarbonyl-$(C_1-C_4)$-alkyl-, $((C_1-C_4)$-alkoxycarbonyl$)$-$(C_1-C_4)$-alkyl-, $R^{11}R^{12}N$—CO—$(C_1-C_4)$-alkyl-, $R^{13}$-$SO_2$—, or aryl;

$R^{11}$ and $R^{12}$ are identical or different residues selected from hydrogen and $(C_1-C_4)$-alkyl;

$R^{13}$ is $(C_1-C_4)$-alkyl, aryl, or $R^{11}R^{12}N$—;

aryl is phenyl, naphthyl, or heteroaryl which can all be substituted by one or more identical or different substituents from the group consisting of halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$ -alkyl, $(C_1-C_2)$-alkylenedioxy, $NH_2$, —NH—$(C_1-C_4)$-alkyl, —N$((C_1-C_4)$-alkyl$)_2$, —NH—CHO, —NH—CO—$(C_1-C_4)$-alkyl, CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO, and —CO—$(C_1-C_4)$-alkyl;

heteroaryl is a residue of a monocyclic 5-membered or 6-membered aromatic heterocycle, or of a bicyclic 8-membered to 10-membered aromatic heterocycle, wherein said heterocycle contains one or more identical or different ring heteroatoms selected from N, O, and S;

m is 0, 1, or 2;

in any stereoisomeric form, or mixtures thereof in any ratio, or their physiologically acceptable salts.

If residues, groups, or substituents can occur several times in the compounds of formula I, they can all independently of one another have the indicated meanings and can in each case all be identical or different unless specifically noted otherwise.

Alkyl residues can be straight-chain or branched. This also applies if they are contained in other groups, for example in alkoxy groups (—O-alkyl groups), alkoxycarbonyl groups, or amino groups, or if they are substituted. Examples of alkyl are methyl, ethyl, propyl, butyl, pentyl, hexyl, heptyl, octyl, nonyl, decyl, the n-isomers of all these residues, isopropyl, isobutyl, isopentyl, sec-butyl, tert-butyl, neopentyl, and 3,3-dimethylbutyl. The term alkyl here is expressly understood as including, in addition to saturated alkyl residues, also unsaturated alkyl residues which contain one or more double bonds, such as alkenyl residues. Examples of such alkyl residues are vinyl, 1-propenyl, 2-propenyl (allyl), 2-butenyl, 2-methyl-2-propenyl, and 3-methyl-2-butenyl. Alkyl residues can be unsubstituted or substituted as indicated. If alkyl residues are substituted by one or more substituents, they are preferably substituted by one, two, or three, in particular by one or two, identical or different substituents. Substituents can be situated in all suitable positions of an alkyl residue.

Examples of cycloalkyl are cyclopropyl, cyclobutyl, cyclopentyl, cyclohexyl, cycloheptyl, cyclooctyl, and cyclononyl, which may be optionally substituted as indicated previously. For example, cycloalkyl may be optionally substituted by one or more identical or different substituents, wherein said substituent is selected from at least one of $(C_1-C_4)$-alkyl (including methyl and isopropyl), hydroxy, acyloxy (including acetyloxy, propionyloxy, butyryloxy, isobutyryloxy and pivaloyloxy), amino, substituted amino groups (including the abovementioned acylamino groups such as acetylamino, and optionally substituted benzoylamino and sulfonylamino groups, like methanesulfonylamino, and optionally substituted benzenesulfonylamino). If cycloalkyl residues are substituted by one or more substituents, they are preferably substituted by one, two, three, or four, in particular by one or two, identical or different substituents. Examples of such substituted cycloalkyl residues are 4-methylcyclohexyl, 4-tert-butylcyclohexyl, 4-hydroxycyclohexyl, 4-acetyloxycyclohexyl, 4-aminocyclohexyl, 4-acetylaminocyclohexyl, 4-ethoxycarbonylaminocyclohexyl, 3-methylcyclopentyl, 3-hydroxycyclopentyl, 3-aminocyclopentyl, or 2,3-dimethylcyclopentyl. Substituents can be situated in all suitable positions of a cycloalkyl residue.

Carbocyclic aryl residues such as phenyl residues and naphthyl residues and heterocyclic aryl residues (=heteroaryl residues), if not stated otherwise, may be unsubstituted, or may carry one or more, i.e., one, two, three, or four, identical or different substituents which may be situated in all suitable positions. If not stated otherwise, the substituents indicated in the definition of the group aryl can occur as substituents in the residues themselves. $(C_1-C_2)$-Alkylenedioxy can, for example, be methylenedioxy or ethylenedioxy. If nitro groups are present as substituents in a compound of formula I, altogether a maximum of only two nitro groups can be present in the molecule. If an aryl residue such as, for example, a phenyl residue carries a further phenyl residue as substituent, the latter phenyl residue can also be unsubstituted or substituted by one or more, for example one, two, three, or four identical or different substituents, in particular by substituents selected from $(C_1-C_4)$-alkyl, halogen, hydroxy, $(C_1-C_4)$-alkoxy, trifluoromethyl, cyano, hydroxycarbonyl, $((C_1-C_4)$-alkoxy)carbonyl, aminocarbonyl, nitro, amino, $(C_1-C_4)$-alkylamino, di-$((C_1-C_4)$-alkyl)amino, and $((C_1-C_4)$-alkyl) carbonylamino.

In monosubstituted phenyl residues, the substituent can be situated in the 2-position, the 3-position, or the 4-position. In disubstituted phenyl residues, the substituents can be situated in 2,3-position, 2,4-position, 2,5-position, 2,6-position, 3,4-position, or 3,5-position. In trisubstituted phenyl residues, the substituents can be situated in 2,3,4-position, 2,3,5-position, 2,3,6-position, 2,4,5-position, 2,4,6-position, or 3,4,5-position. Naphthyl can be 1-naphthyl or 2-naphthyl. In monosubstituted 1-naphthyl residues the substituent can be situated in the 2-position, the 3-position, the 4-position, the 5-position, the 6-position, the 7-position, or the 8-position, in monosubstituted 2-naphthyl residues in the 1-position, the 3-position, the 4-position, the 5-position, the 6-position, the 7-position, or the 8-position. In polysubstituted naphthyl residues, for example di- or trisubstituted naphthyl residues, the substituents can also be situated in all suitable positions.

Unless stated otherwise, heteroaryl residues, residues of saturated heterocyclic rings and residues of rings which are formed by two groups bonded to a nitrogen atom together with this nitrogen atom are preferably derived from heterocycles which contain one, two, three, or four identical or different ring heteroatoms, more preferably from heterocycles which contain one, two, or three, particular preferably one or two, identical or different ring heteroatoms. If not stated otherwise, the heterocycles can be monocyclic or polycyclic, for example monocyclic, bicyclic, or tricyclic. Preferably, they are monocyclic or bicyclic, in particular monocyclic. The individual rings preferably contain 5, 6, or 7 ring members. Examples of monocyclic and bicyclic heterocyclic systems from which residues occurring in the compounds of formula I can be derived are pyrrole, furan, thiophene, imidazole, pyrazole, 1,2,3-triazole, 1,2,4-triazole, 1,3-dioxole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxin, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, quinoline, isoquinoline, cinnoline, quinazoline, quinoxaline, phthalazine, thienothiophenes, 1,8-naphthyridine and other naphthyridines, pteridine, and phenothiazine, all in each case in saturated form (perhydro form) or in partially unsaturated form (for example dihydro form or tetrahydro form) or in maximally unsaturated or aromatic form, if the forms concerned are known and stable. Thus, the heterocycles which are suitable also include the saturated heterocycles pyrrdlidine, piperidine, perhydroazepine (=hexamethyleneimine), piperazine, morpholine, 1,3-thiazolidine and thiomorpholine which—if this is in accord with the respective definition—are examples of residues of saturated heterocyclic rings and of residues of rings which are formed by two groups bonded to a nitrogen atom together with this nitrogen atom. The degree of saturation of heterocyclic groups is indicated in the individual definitions. Unsaturated heterocycles can contain one, two, or three double bonds in a ring. Five-membered and six-membered rings in these monocyclic and polycyclic heterocycles can also be aromatic.

Heterocyclic residues may be bonded via any suitable ring carbon atom. Nitrogen heterocycles, i.e., pyrrole, imidazole, pyrrolidine, piperidine, hexamethyleneimine, 1,3-thiazolidine, morpholine, thiomorpholine, piperazine, etc., also may be bonded via any suitable ring nitrogen atom, in particular if the nitrogen heterocycle is bonded to a carbon atom. For example, thienyl can be present as 2-thienyl or 3-thienyl, furyl as 2-furyl or 3-furyl, piperidyl as 1-piperidyl (=piperidino), 2-piperidyl, 3-piperidyl, or 4-piperidyl, (thio)morpholinyl as 2-(thio)morpholinyl, 3-(thio)morpholinyl, or 4-(thio)morpholinyl (=(thio)morpholino). A residue which is derived from 1,3-thiazole can be bonded via the 2-position, the 3-position, the 4-position, or the 5-position, a residue which is derived from imidazole can be bonded via the 1-position, the 2-position, the 4-position, or the 5-position. Pyridyl can be 2-pyridyl, 3-pyridyl, or 4-pyridyl. Unless stated otherwise, the heterocyclic groups can be unsubstituted or may be substituted with one or more, for example one, two, three, or four, in particular one or two, identical or different substituents. The substituents in heterocycles can be situated in any desired suitable position or positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridyl residue in the 3-position and/or in the 4-position and/or in the 5-position and/or in the 6-position, in a 3-pyridyl residue in the 2-position and/or in the 4-position and/or in the 5-position and/or in the 6-position, in a 4-pyridyl residue in the 2-position and/or in the 3-position and/or in the 5-position and/or in the 6-position.

Unless stated otherwise, the substituents which can occur in heterocycles can be, for example, the substituents indicated in the definition of the group aryl, and in the case of saturated or partially unsaturated heterocycles further substituents can also be the oxo group (=O) and the thioxo group (=S). Two substituents on a heterocycle and appropriate substituents on a carbocycle can also form a ring, i.e., further rings can be fused to a ring system such that cyclopenta-fused, cyclohexa-fused or benzo-fused rings, for example, may be present. Unless stated otherwise, possible substituents on a suitable ring nitrogen atom of a heterocycle are unsubstituted and substituted $(C_1-C_4)$-alkyl, aryl, acyl such as —CO—$(C_1-C_4)$-alkyl, or —CO-aryl, or sulfonyl groups such as —$SO_2$—$(C_1-C_4)$-alkyl or —$SO_2$-aryl. Suitable sulfur heterocycles can also be present as S-oxides or S,S-dioxides, i.e., instead of a sulfur atom the group S(=O) or the group S(=O)$_2$ may be a member of the ring. Suitable nitrogen atoms in compounds of formula I can also be present as N-oxides or as quaternary salts with an anion derived from a physiologically acceptable acid as counterion. Pyridyl groups can be present, for example, as pyridine N-oxides.

Halogen is fluorine, chlorine, bromine, or iodine, preferably fluorine or chlorine. The present invention includes all stereoisomeric forms of compounds of formula I.

Asymmetric centers present in compounds of formula I may independently of one another have S configuration or R configuration. The invention includes all possible enantiomers and diastereomers, as well as mixtures of two or more stereoisomeric forms, such as mixtures of enantiomers and/or diastereomers, in any ratio. The invention thus relates to enantiomers in enantiomerically pure form, both as dextrorotatory and as levorotatory antipodes, in the form of racemates and in the form of mixtures of the two enantiomers in any ratio. In the presence of cis/trans isomerism, such as in cycloalkyl groups, the invention relates both to the cis form and the trans form, and mixtures of these forms in any ratio. Individual stereoisomers can be prepared, if desired, by resolution of a mixture according to customary methods, for example, by chromatography or crystallization, by use of stereochemically homogeneous starting substances in the synthesis, or by stereoselective synthesis. If appropriate, a derivatization can be carried out before separation of stereoisomers. The separation of a stereoisomeric mixture may be carried out at the stage of the compounds of formula I or at the stage of an intermediate in the course of the synthesis. If mobile hydrogen atoms are present, the present invention also includes all tautomeric forms of compounds of formula I.

The present invention also relates to physiologically acceptable or toxicologically acceptable salts, in particular pharmaceutically utilizable salts, of compounds of formula I which contain one or more acidic and/or basic groups. Thus, in compounds of formula I containing acidic groups, these groups can be present, for example, as alkali metal salts, alkaline earth metal salts or as ammonium salts and can be used according to the invention. Examples of such salts are sodium salts, potassium salts, calcium salts, magnesium salts, salts with physiologically acceptable quaternary ammonium ions or acid addition salts with ammonia or organic amines, for example with ethylamine, ethanolamine, triethanolamine, or amino acids. Compounds of formula I which contain one or more basic, i.e., protonatable, groups may be present in the form of their acid addition salts with physiologically acceptable inorganic or organic acids and can be used according to the invention, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid, etc. If compounds of formula I simultaneously contain acidic and basic groups in the molecule, in addition to the salt forms outlined above, the invention also includes internal salts or betaines (zwitterions). Salts can be obtained from compounds of formula I by customary processes known to the person skilled in the art, such as by combination with an organic or inorganic acid or base in a solvent or diluent or alternatively from other salts by anion exchange or cation exchange. The present invention also includes all salts of compounds of formula I which, because of low physiological tolerability, are not directly suitable for use in pharmaceuticals, but are suitable, for example, as intermediates for chemical reactions or for the preparation of physiologically acceptable salts.

The present invention furthermore includes all solvates and addition compounds of compounds of formula I, in particular physiologically acceptable ones, for example, hydrates or adducts with alcohols, and also derivatives of compounds of formula I such as, for example, esters, prodrugs, and active metabolites.

Preferably, one of the residues $R^1$ and $R^2$ is $(C_1-C_8)$-alkyl which can be substituted by one or more identical or different substituents selected from hydroxy, $(C_1-C_4)$-alkoxy, $(C_1-C_4)$-alkyl-S(O)$_m$—, $(C_3-C_7)$-cycloalkyl, phenyl, and naphthyl, or is $(C_3-C_9)$-cycloalkyl optionally substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, where phenyl groups, naphthyl groups, and benzyl groups present in the residues $R_1$ and $R^2$ may be unsubstituted or substituted on the aromatic ring. Preferably, the other of the residues $R^1$ and $R^2$ is hydrogen, or is $(C_1-C_8)$-alkyl which can be substituted by one or more identical or different substituents selected from hydroxy, $(C_1-C_4)$-alkoxy, $(C_1-C_4)$-alkyl-S(O)$_m$—, $(C_3-C_7)$-cycloalkyl, phenyl, and naphthyl, or is $(C_3-C_9)$-cycloalkyl optionally substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, where phenyl groups, naphthyl groups, and benzyl groups present in the residues $R^1$ and $R^2$ can be unsubstituted or substituted on the aromatic ring.

Compounds of particular interest in the present invention are those where one of the residues $R^1$ and $R^2$ is $(C_1-C_8)$-alkyl or is $(C_3-C_9)$-cycloalkyl and the other of the residues $R^1$ and $R^2$ is hydrogen, or if both residues $R^1$ and $R^2$ are identical or different $(C_1-C_8)$-alkyl groups, where all alkyl groups and cycloalkyl groups can be unsubstituted or substituted as indicated previously. It is especially preferred if one of the residues $R^1$ and $R^2$ is $(C_3-C_9)$-cycloalkyl which is unsubstituted or substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH, $(C_1-C_4)$-alkyl-O—CO—NH—, phenyl-CO—NH—, $(C_1-C_4)$-alkyl-SO$_2$—NH—, and phenyl-SO$_2$—NH—, where phenyl groups and benzyl groups present in the residues $R^1$ and $R^2$ can be unsubstituted or substituted on the aromatic ring, and the other of the residues $R^1$ and $R^2$ is hydrogen.

If one of the residues $R^1$ and $R^2$ is $(C_3-C_9)$-cycloalkyl optionally substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$- alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, or is a residue of a 5-membered to 7-membered saturated heterocyclic ring which contains one or two identical or different heteroatom ring members selected from O, NR$^{10}$, and S(O)$_m$ and which can be substituted by one or more identical or different substituents selected from $(C_1-C_4)$-alkyl, hydroxy, and aryl-$(C_1-C_4)$-alkyl-, then the other of the residues R$^1$ and R$^2$ is preferably hydrogen.

An alkyl residue representing R$^1$ or R$^2$ is preferably an unsubstituted or substituted $(C_1-C_4)$-alkyl residue. A $(C_3-C_9)$-cycloalkyl residue representing R$^1$ or R$^2$ is preferably an unsubstituted or substituted $(C_3-C_7)$-cycloalkyl residue from cyclopropyl, cyclobutyl, cyclopentyl, cyclohexyl and cycloheptyl, particularly preferably an unsubstituted or substituted $(C_5-C_6)$-cycloalkyl residue selected from cyclopentyl and cyclohexyl. If a cycloalkyl residue representing R$^1$ or R$^2$ is substituted, it is preferably substituted by one or more substituents selected from $(C_1-C_4)$-alkyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, where phenyl groups present in the residues R$^1$ and R$^2$ can be unsubstituted or substituted. Particularly preferably, a substituted cycloalkyl residue representing R$^1$ or R$^2$ is substituted by one or more substituents selected from $(C_1-C_4)$-alkyl, hydroxy, amino, $(C_1-C_4)$-alkyl-CO—O—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, where phenyl groups present in the residues R$^1$ and R$^2$ can be unsubstituted or substituted. Especially preferably, a cycloalkyl residue representing R$^1$ or R$^2$ is substituted by one or more $(C_1-C_4)$-alkyl residues or by a hydroxy group or by an amino group, in particular by a hydroxy group.

A residue of a 5-membered to 7-membered saturated heterocyclic ring representing R$^1$ or R$^2$ preferably contains one heteroatom ring member selected from O, NR$^{10}$, and S(O)$_m$, particularly preferably a group NR$^{10}$, as a heteroatom ring member. Preferably, a heterocyclic ring of this type is bonded via a ring carbon atom which is not directly adjacent to a heteroatom ring member. Examples of residues of heterocyclic rings of this type are optionally substituted pyrrolidinyl (such as 3-pyrrolidinyl), optionally substituted piperidyl (such as 3-piperidyl or 4-piperidyl), tetrahydrofuryl (such as 3-tetrahydrofuryl), tetrahydrothienyl and its S-oxide and S,S-dioxide, (such as 3-tetrahydrothienyl), or tetrahydro(thio)pyranyl.

In addition to the abovementioned meanings of R$^1$ and R$^2$, it is furthermore preferred if the residue R$^1$R$^2$N— is a residue of a 5-membered, 6-membered or 7-membered saturated heterocyclic ring which is bonded via a ring nitrogen atom and which, in addition to the nitrogen atom bonded to the tetrahydroquinazoline ring, may contain one oxygen atom or one group S(O)$_m$ as a further heteroatom ring member and is optionally substituted by one or more identical or different substituents selected from $(C_1-C_4)$-alkyl, hydroxy, $(C_1-C_4)$-alkoxy, hydroxy-$(C_1-C_4)$-alkyl- and R$^{11}$R$^{12}$N—. A residue of a heterocyclic ring representing R$^1$R$^2$N— is preferably derived from a 5-membered or 6-membered saturated heterocyclic ring, particularly preferably from piperidine, morpholine, or thiomorpholine (and its S-oxide and S,S-dioxide) which are optionally substituted as indicated. Of particular interest are compounds with residues derived from unsubstituted piperidine, morpholine, or thiomorpholine (and its S-oxide and S,S-dioxide).

The aryl group representing R$^3$ preferably is substituted phenyl, which is substituted as indicated above for substituted aryl, particularly preferably phenyl which is substituted by one or two identical or different substituents from those indicated above for aryl. Especially preferably, R$^3$ is phenyl which is substituted by one or two substituents selected from halogen, —O—$(C_1-C_4)$-alkyl and $(C_1-C_4)$-alkyl, in particular selected from halogen and $(C_1-C_4)$-alkyl, moreover preferably phenyl which is substituted by substituents selected from fluorine, chlorine, and methyl. The substituent in a monosubstituted phenyl group representing R$^3$ is preferably in the meta-position or para-position.

Aryl is preferably phenyl or 5-membered or 6-membered monocyclic heteroaryl having one or two, in particular one, ring heteroatom selected from N, O, and S which can be substituted as indicated above, particularly preferably unsubstituted or substituted phenyl or unsubstituted pyridyl, thienyl, or furyl, very particularly preferably unsubstituted or substituted phenyl or unsubstituted pyridyl.

Preferred compounds of formula I are those in which one or more of the residues contained therein have the meanings of particular interest as indicated above. The present invention relates to all combinations of preferred definitions of residues and substituents and/or of one or more specific meanings of residues and substituents which are indicated in their definitions or in the additional explanations on residues, substituents and groups. Also with respect to all preferred compounds of formula I the present invention comprises any stereoisomeric form, physiologically acceptable salt, or a mixture thereof in any ratio.

The present invention also relates to processes for the preparation of compounds of formula I which are explained below and by which the compounds according to the invention are obtainable. Compounds of formula I can be prepared by first reacting an amidine of formula II in an manner known per se with a 2-oxocyclohexanecarboxylic acid ester of formula III to give a 4-hydroxytetrahydroquinazoline of formula IV (see Scheme 1 below). The residue R in formula III is, for example, $(C_1-C_4)$-alkyl such as methyl or ethyl. The residues R$^1$, R$^2$ and R$^3$ in formulae II, IV, V, and VI have the meanings indicated above for formula I. The hydroxytetrahydroquinazoline of formula IV is then activated, for example, by conversion into a 2-aryl-4-halo-5,6,7,8-tetrahydroquinazoline. For example, compounds of formula IV can be converted into the 4-chlorotetrahydroquinazolines of formula V by reaction with a phosphorus halide such as phosphorus oxychloride. By reaction of a compound of formula V (or of another reactive derivative of the hydroxytetrahydroquinazoline) with the desired amine of formula VI the compound of formula I according to the invention is then obtained with replacement of the chlorine by the amino group. Suitable solvents for this replacement reaction are, for example, water, alcohols such as methanol, ethanol or isopropanol, ethers such as tetrahydrofuran or dioxane, amides such as dimethylformamide (DMF) or N-methylpyrrolidone (NMP), or hydrocarbons or halogenated hydrocarbons such as benzene, toluene, xylene, chlorobenzene or dichlorobenzene.

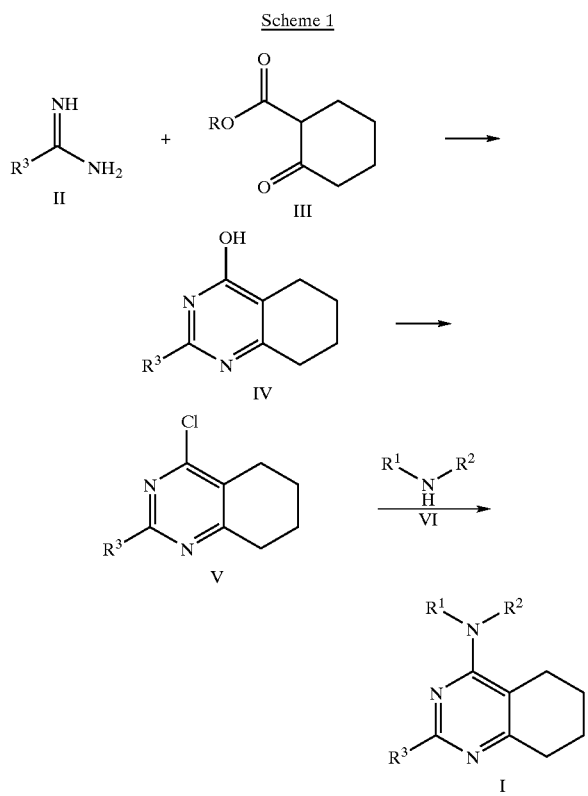

Scheme 1

The above reactions can be carried out in a wide temperature range. Reaction temperatures from about 20° C. to about 150° C. are preferred. The reactions can be accelerated by addition of suitable bases such as sodium bicarbonate, sodium carbonate, potassium carbonate, alkali metal alkoxides (such as sodium alkoxides or potassium alkoxides), or amines (such as triethylamine or pyridine), specifically, the first and in the last step additionally may be accelerated by excess amidine or amine, respectively. Instead of the free amidines of formula II, the corresponding amidinium salts (such as amidinium hydrochlorides) can also be employed. In this case, it is particularly convenient to carry out the first step with addition of a base. Likewise, the amines of formula VI employed in the last step can also be employed in the form of salts which are converted into the free amines in situ or in a separate step using a base. The intermediates of formulae IV and V and the final compounds of formula I can be separated from the respective reaction mixture by customary processes such as extraction, crystallization, sublimation, chromatography, or distillation and, if desired, purified, but depending on the circumstances of the individual case the intermediates can also be reacted further without intermediary isolation. Moreover, functional groups in the compounds obtained can be subject to conversion reactions. For example, thioether groups can be converted into sulfones or sulfoxides by oxidation with a peroxy compound such as 3-chloroperbenzoic acid, monoperoxyphthalic acid, or hydrogen peroxide, or carboxylic acid ester groups can be hydrolyzed to the carboxylic acids or converted into amides, or acylations can be carried out.

All reactions for the synthesis of the compounds of formula I are well known per se to the person skilled in the art and can be carried out under standard conditions according to, or analogously to, literature procedures such as are described, for example, in Houben-Weyl, *Methoden der Organischen Chemie* (*Methods of Organic Chemistry*), Thieme-Verlag, Stuttgart, or *Organic Reactions*, John Wiley & Sons, New York. Depending on the circumstances of the individual case, it may also be advantageous or necessary for the avoidance of side reactions during the synthesis of the compounds of formula I to temporarily block certain functional groups by the introduction of protective groups and then later to liberate them again or at first to employ functional groups in the form of precursor groups from which the desired functional groups are then produced in later steps. Such synthesis strategies and the protective groups or precursors suitable for the individual case are known to the person skilled in the art. The starting amidines of formula II or their salts, the oxoesters of formula III and the amines of formula VI are commercially available or can be prepared by, or analogously to, well known processes.

The compounds of formula I according to the invention bring about an increase in the cGMP concentration by means of the activation of soluble guanylate cyclase (sGC) and are therefore valuable agents for the therapy and prophylaxis of diseases which are associated with a low or reduced cGMP level or are caused by such a level, or for whose therapy or prophylaxis an increase in the CGMP level that is present is desired. One investigative method for the activation of sGC by compounds of formula I is the activity assay described below. Preferred substances of formula I are those which exhibit in this assay at least a three-fold stimulation of the sGC activity as compared to control levels.

Diseases and pathological conditions which are associated with a low cGMP level or in which an increase in the cGMP level is desirable and for whose therapy and prophylaxis compounds of formula I can be employed are, for example, cardiovascular disorders such as endothelial dysfunction, diastolic dysfunction, atherosclerosis, hypertension, stable and unstable angina pectoris, thromboses, restenoses, myocardial infarcts, strokes, cardiac insufficiency or pulmonary hypertension, erectile dysfunction, bronchial asthma, chronic renal insufficiency, and diabetes. Compounds of formula I can moreover be employed in the therapy of liver cirrhosis and for improving restricted learning capacity or memory power.

Compounds of formula I and their physiologically acceptable salts can thus be used in animals, preferably in mammals, and in particular in humans, as pharmaceuticals on their own, in mixtures with one another or in the form of pharmaceutical compositions. The present invention therefore also relates to compounds of formula I and their physiologically acceptable salts for use as pharmaceuticals or medicaments, their use for the normalization of a disturbed cGMP balance and in particular their use in the therapy and prophylaxis of the abovementioned diseases and conditions, and their use for the production of pharmaceutical compositions therefor. The present invention furthermore relates to pharmaceutical compositions or pharmaceutical preparations which contain an efficacious dose of at least one compound of formula I and/or of its/their physiologically acceptable salts as an active constituent and a physiologically acceptable carrier. The pharmaceuticals according to the invention can be administered orally, for example in the form of pills, tablets, film-coated tablets, coated tablets, granules, hard and soft gelatin capsules, aqueous, alcoholic or oily solutions, syrups, emulsions or suspensions, or rectally, for example in the form of suppositories. The administration can also be carried out parenterally, for example subcutaneously, intramuscularly or intravenously in the form of injection solutions or infusion solutions. Further possible administration forms are percutaneous or topical application, such as ointments, tinctures, sprays, or transdermal therapeutic systems, or administration by inhalation in the form of nasal sprays or aerosol mixtures or administration in the form of microcapsules, implants, or rods. The preferred administration form depends on various factors known to those of skill in the art, such as consideration of the disease to be treated and its severity as well as other factors discussed below.

The pharmaceutical compositions normally contain approximately 0.2 to 1000 mg, preferably 0.2 to 500 mg, in particular 1 to 200 mg, of at least one active compound of formula I and/or its physiologically acceptable salts and a physiologically acceptable carrier, i.e., one or more physiologically acceptable and pharmaceutically suitable vehicles and/or additives. The pharmaceutical compositions can be produced in a manner known per se. For this, one or more compounds of formula I and/or their physiologically acceptable salts are brought, together with one or more solid or liquid pharmaceutical vehicles and/or additives and, if desired, with one or more other pharmaceutical active compounds having therapeutic or prophylactic action, into a suitable administration form and dosage form which can then be used as a pharmaceutical in human or veterinary medicine. The pharmaceutical compositions normally contain 0.5 to 90% by weight of at least one compound of formula I and/or their physiologically acceptable salts.

For the production, for example, of pills, tablets, coated tablets and hard gelatin capsules, lactose, starch, for example corn starch, or starch derivatives, talc, stearic acid or its salts, etc. can be used. Vehicles for soft gelatin capsules and suppositories are, for example, fats, waxes, semisolid and liquid polyols, natural or hardened oils, etc. Suitable vehicles for the preparation of solutions, for example injection solutions, or of emulsions or syrups are, for example, water, physiological saline solution, alcohols such as ethanol, glycerol, polyols, sucrose, invert sugar, glucose, mannitol, vegetable oils, etc. Compounds of formula I and their physiologically acceptable salts can also be lyophilized and the lyophilizates obtained be used, for example, for the production of injection solutions or infusion solutions. Suitable vehicles for microcapsules, implants or rods are, for example, copolymers of glycolic acid and lactic acid.

In addition to the active compounds and vehicles, the pharmaceutical compositions optionally may additionally contain customary additives or auxiliaries, such as fillers, disintegrants, binders, lubricants, wetting agents, stabilizers, emulsifiers, dispersants, preservatives, sweetening agents, colorants, flavorings, aromatizers, thickening agents, diluents, buffer substances, solvents, solubilizers, agents for achieving a depot effect, salts for altering the osmotic pressure, coating agents, and/or antioxidants.

The dose of the active compound(s) of formula I and/or its physiologically acceptable salt to be administered depends on the individual case and is to be suited to the individual conditions as customary for optimal action. Thus it depends, for example, on the nature and severity of the disease to be treated, on the sex, age, weight, and individual responsiveness of the human or animal to be treated, on the potency and duration of action of the specific compound employed, on whether the therapy is acute or chronic or prophylaxis is carried out, or on whether further active compounds are administered in addition to compounds of formula I . In general, a daily dose of approximately 0.01 to 100 mg/kg, preferably 0.1 to 10 mg/kg, in particular 0.3 to 5 mg/kg (in each case mg per kg of body weight) is appropriate in the case of administration to an adult of about 75 kg in weight to achieve the desired action. The daily dose can be administered in a single dose or, in particular in the case of administration of relatively large amounts, be divided into a number of individual doses, for example two, three, or four doses. Depending on individual behavior, it may be necessary to deviate upward or downward from the daily dose indicated.

Compounds of formula I activate soluble guanylate cyclase. On account of this property, apart from as pharmaceutical active compounds in human medicine and veterinary medicine, they can also be used as a scientific tool or as an aid for biochemical investigations in which an effect on guanylate cyclase of this type is intended, and also for diagnostic purposes, for example in the in vitro diagnosis of cell or tissue samples. In addition, compounds of formula I and their salts, as already mentioned above, can serve as intermediates for the preparation of further pharmaceutical active compounds.

The following examples illustrate the invention without restricting it.

EXAMPLES

Example 1

2-(4-Chlorophenyl)-4-hydroxy-5,6,7,8-tetrahydroquinazoline 7.5 g of ethyl 2-oxocyclohexane-4-carboxylate and 9.6 g of 4-chlorobenzamidine hydrochloride were introduced into 50 ml of methanol. 5.6 g of potassium tert-butylate were added with stirring. The reaction mixture was stirred under reflux for 4 hours and then poured onto ice water. The crystalline product was filtered off with suction, washed with water and recrystallized from dimethylformamide. Yield: 8.8 g; m.p.: >300° C.

The intermediates of Examples 2 to 12 were prepared analogously to Example 1.

Example 2

2-(3-Chlorophenyl)4-hydroxy-5,6,7,8-tetrahydroquinazoline; m.p.: 239° C.

Example 3

2-(4-Methoxyphenyl)4-hydroxy-5,6,7,8-tetrahydroquinazoline; m.p.: 245° C.

Example 4

2-(3,5-Dichlorophenyl)4-hydroxy-5,6,7,8-tetrahydroquinazoline; m.p.: 265° C.

Example 5

2-(2,4-Dichlorophenyl)-4-hydroxy-5,6,7,8-tetrahydroquinazoline; m.p.: 232° C.

Example 6

2-(3,4-Dichlorophenyl)-4-hydroxy-5,6,7,8-tetrahydroquinazoline; m.p.: 271° C.

Example 7

2-(2-Chlorophenyl)4-hydroxy-5,6,7,8-tetrahydroquinazoline; m.p.: 181° C.

Example 8

2-(4-Aminocarbonylphenyl)-4-hydroxy-5,6,7,8-tetrahydroquinazoline; m.p.: 270° C.

Example 9

2-(4-Methylphenyl)-4-hydroxy-5,6,7,8-tetrahydroquinazoline; m.p.: 263° C.

Example 10

2-(3,4-Dimethoxyphenyl)-4-hydroxy-5,6,7,8-tetrahydroquinazoline; m.p.: 225° C.

Example 11

2-(3-Bromophenyl)4-hydroxy-5,6,7,8-tetrahydroquinazoline; m.p.: 246° C.

Example 12

2-(3,5-Difluorophenyl)-4-hydroxy-5,6,7,8-tetrahydroquinazoline; m.p.: 250° C.

Example 13

2-(4-Chlorophenyl)4-chloro-5,6,7,8-tetrahydroquinazoline 8.0 g of 2-(4-chlorophenyl)4-hydroxy-5,6,7,8-tetrahydroquinazoline were heated to 100° C. in 10 ml of phosphorus oxychloride. After 3 hours, the cooled solution was carefully poured onto ice water. The crystalline product was filtered off with suction, washed well with water and dried in vacuo at room temperature. Yield: 6.2 g; m.p.: 121° C.

The intermediates of Examples 14 to 24 were prepared analogously to Example 13.

Example 14

2-(3-Chlorophenyl)-4-chloro-5,6,7,8-tetrahydroquinazoline; m.p.: 121° C.

Example 15

2-(4-Methoxyphenyl)-4-chloro-5,6,7,8-tetrahydroquinazoline; m.p.:112° C.

Example 16

2-(3,5-Dichlorophenyl)-4-chloro-5,6,7,8-tetrahydroquinazoline; m.p.: 183° C.

Example 17

2-(2,4-Dichlorophenyl)4-chloro-5,6,7,8-tetrahydroquinazoline; m.p.: 111° C.

Example 18

2-(3,4-Dichlorophenyl)-4-chloro-5,6,7,8-tetrahydroquinazoline; m.p.: 138° C.

Example 19

2-(2-Chlorophenyl)4-chloro-5,6,7,8-tetrahydroquinazoline; m.p.: 76° C.

Example 20

2-(4-Cyanophenyl)4-chloro-5,6,7,8-tetrahydroquinazoline

The compound was obtained from 2-(4-aminocarbonylphenyl)4-hydroxy-5,6,7,8-tetrahydroquinazoline (Example 8) by the procedure of Example 13. M.p.: 190° C.

Example 21

2-(4-Methylphenyl)4-chloro-5,6,7,8-tetrahydroquinazoline; m.p.: 117° C.

Example 22

2-(3,4-Dimethoxyphenyl)-4-chloro-5,6,7,8-tetrahydroquinazoline; m.p.: 146° C.

Example 23

2-(3-Bromophenyl)-4-chloro-5,6,7,8-tetrahydroquinazoline; m.p.: 93° C.

Example 24

2-(3,5-Difluorophenyl)-4-chloro-5,6,7,8-tetrahydroquinazoline; m.p.: 130° C.

Example 25

2-(4-Chlorophenyl)4-cyclopentylamino-5,6,7,8,7-tetrahydroquinazoline 0.25 g of 2-(4-chlorophenyl)-4-chloro-5,6,7,8-tetrahydroquinazoline, 0.4 g of cyclopentylamine and 1 ml of N—methylpyrrolidone were heated in an oil bath to 130° C. After 5 hours the mixture was diluted with 20 ml of water and stirred at room temperature. The precipitated product was filtered off with suction, washed with water and dried in vacuo at 40° C. Yield: 0.23 g; m.p.: 128° C.

Example 26

2-(4-Chlorophenyl)4-(trans-4-hydroxycyclohexylamino)-5,6,7,8-tetrahydroquinazoline methanesulfonic acid salt 0.15 g of 2-(4-chlorophenyl)4-chloro-5,6,7,8-tetrahydroquinazoline, 0.39 g of trans-4-aminocyclohexanol hydrochloride, 0.18 g of potassium tert-butylate and 1.5 ml of N-methylpyrrolidone were heated in an oil bath at 130° C. for 2 hours. 15 ml of water were added to the cooled solution and the precipitated product was filtered off with suction. The dried solid was taken up in 8 ml of ethyl acetate and 2 ml of isopropanol and treated with methanesulfonic acid. The precipitated product was filtered off with suction, washed with ethyl acetate and dried in vacuo at 40° C. Yield: 0.13 g; m.p.: 224° C.

The compounds of formula I of Examples 27 to 114 in Table 1 below were prepared analogously to Examples 25 and 26.

TABLE 1

| Example | $R^3$ (in formula I) | $R^1R^2N-$ (in formula I) | M.p. (° C.) |
|---|---|---|---|
| 27 | 4-chlorophenyl | trans-4-hydroxycyclohexylamino | 219 |
| 28 | 4-chlorophenyl | 2-hydroxyethylamino | 186 |
| 29 | 4-chlorophenyl | butylamino | 107 |
| 30 | 4-chlorophenyl | 2-(3-methoxyphenyl)ethylamino | oil |
| 31 | 4-chlorophenyl | dipropylamino | 92 |
| 32 | 4-chlorophenyl | cis-2,6-dimethylmorpholino | 141 |
| 33 | 4-chlorophenyl | 5-hydroxy-1,5-dimethylhexylamino | oil |
| 34 | 4-chlorophenyl | 4-hydroxybutylamino | 138 |
| 35 | 4-chlorophenyl | 4-hydroxypiperidino | 149 |
| 36 | 4-chlorophenyl | cis/trans-4-hydroxycyclohexylamino | 185 |
| 37 | 4-chlorophenyl | 4-acetyloxycyclohexylamino | 195 |
| 38 | 4-chlorophenyl | trans-4-aminocyclohexylamino | 251 |
| 39 | 4-chlorophenyl | trans-4-acetylaminocyclohexylamino | 301 (dec.) |
| 40 | 4-chlorophenyl | trans-4-methanesulfonylamino-cyclohexylamino | 224 |
| 41 | 4-chlorophenyl | trans-4-(4-chlorophenylsulfonylamino)-cyclohexylamino | 230 |

TABLE 1-continued

| Example | R³ (in formula I) | R¹R²N- (in formula I) | M.p. (° C.) |
|---|---|---|---|
| 42 | 4-chlorophenyl | trans-4-ethoxycarbonylamino-cyclohexylamino | 305 (dec.) |
| 43 | 4-chlorophenyl | trans-4-benzoylaminocyclohexylamino | 310 |
| 44 | 4-methylphenyl | dipropylamino | 58 |
| 45 | 4-methylphenyl | butylamino | 108 |
| 46 | 4-methylphenyl | thiomorpholino | 185 |
| 47 | 4-methylphenyl | diethylamino | 107 |
| 48 | 4-methylphenyl | 2-hydroxyethylamino | 164 |
| 49 | 4-methylphenyl | cis-2,6-dimethylmorpholino | 135 |
| 50 | 4-methylphenyl | 3-methoxypropylamino | oil |
| 51 | 4-methylphenyl | perhydro-1-azepinyl | 91 |
| 52 | 4-methylphenyl | di-(2-methoxyethyl)amino | oil |
| 53 | 4-methylphenyl | isobutylamino | oil |
| 54 | 4-methylphenyl | cyclopentylamino | 130 |
| 55 | 4-methylphenyl | piperidino | 125 |
| 56 | 4-methylphenyl | cyclopentylamino | 190 (mes.) |
| 57 | 4-methylphenyl | pyrrolidino | 139 |
| 58 | 4-methylphenyl | di-(2-hydroxyethyl)amino | resin |
| 59 | 4-methylphenyl | trans-4-hydroxycyclohexylamino | 185 |
| 60 | 4-methylphenyl | (cyclopropylmethyl)amino | 140 |
| 61 | 4-methylphenyl | cyclobutylamino | 294 |
| 62 | 4-methylphenyl | 4-methylcyclohexylamino | 122 |
| 63 | 4-methylphenyl | N-methyl-N-cyclohexylamino | 141 |
| 64 | 4-methylphenyl | cyclononylamino | oil |
| 65 | 4-methylphenyl | 2-isopropyl-5-methylcyclohexylamino | oil |
| 66 | 4-methylphenyl | trans-2-hydroxycyclohexylamino | 180 |
| 67 | 4-methylphenyl | 3,3-dimethylpiperidino | 79 |
| 68 | 4-methylphenyl | 3-hydroxymethylpiperidino | 140 |
| 69 | 4-methylphenyl | cyclopropylamino | 110 |
| 70 | 4-methylphenyl | (R)-1-phenylethylamino | oil |
| 71 | 4-methylphenyl | (S)-1-phenylethylamino | oil |
| 72 | 3,4-dimethoxyphenyl | cyclohexylamino | 107 |
| 73 | 3,4-dimethoxyphenyl | cyclopentylamino | 237 (HCl) |
| 74 | 3,4-dimethoxyphenyl | trans-4-hydroxycyclohexylamino | 208 (HCl) |
| 75 | 3,4-dimethoxyphenyl | 4-hydroxy-4-phenylpiperidino | 104 |
| 76 | 3,4-dimethoxyphenyl | 4-hydroxybutylamino | 216 (HCl) |
| 77 | 3,4-dimethoxyphenyl | perhydro-1-azepinyl | oil |
| 78 | 3,4-dimethoxyphenyl | butylamino | 211 (HCl) |
| 79 | 3,4-dimethoxyphenyl | dipropylamino | 163 (HCl) |
| 80 | 3,4-dimethoxyphenyl | cis-2,6-dimethylmorpholino | 141 |
| 81 | 3-chlorophenyl | isobutylamino | 89 |
| 82 | 3-chlorophenyl | cyclopentylamino | 111 |
| 83 | 3-chlorophenyl | 2,2,6,6-tetramethylpiperidin-4-ylamino | 165 |
| 84 | 3-chlorophenyl | thiomorpholino | 150 |
| 85 | 3-chlorophenyl | trans-4-hydroxycyclohexylamino | 140 |
| 86 | 3-chlorophenyl | trans-4-hydroxycyclohexylamino | 247 (mes.) |
| 87 | 4-methoxyphenyl | methylamino | 97 |
| 88 | 4-methoxyphenyl | 2-methoxyethylamino | 99 |
| 89 | 4-methoxyphenyl | isopentylamino | 95 |
| 90 | 4-methoxyphenyl | trans-4-hydroxycyclohexylamino | 175 |
| 91 | 4-methoxyphenyl | cyclopentylamino | 110 |
| 92 | 4-methoxyphenyl | 4-hydroxy-4-(4-chlorophenyl)piperidino | 74 |
| 93 | 4-methoxyphenyl | 5-hydroxy-1,5-dimethylhexylamino | oil |
| 94 | 4-cyanophenyl | 2-(2-chlorophenyl)ethylamino | 157 |
| 95 | 4-cyanophenyl | 3,4-dimethoxybenzylamino | 177 |
| 96 | 4-cyanophenyl | trans-4-hydroxycyclohexylamino | 233 |
| 97 | 3,5-dichlorophenyl | trans-4-hydroxycyclohexylamino | 202 |
| 98 | 3,5-dichlorophenyl | cyclohexylamino | 158 |
| 99 | 3,5-dichlorophenyl | N-methyl-N-(trans-4-hydroxycyclohexyl)amino | 170 |
| 100 | 3,5-dichlorophenyl | 4-hydroxybutylamino | 113 |
| 101 | 3,4-dichlorophenyl | trans-4-hydroxycyclohexylamino | 212 |
| 102 | 3,4-dichlorophenyl | cycloheptylamino | 148 |
| 103 | 3,4-dichlorophenyl | 4-hydroxybutylamino | 148 |
| 104 | 2,4-dichlorophenyl | cyclopentylamino | 101 |
| 105 | 2,4-dichlorophenyl | trans-4-hydroxycyclohexylamino | 102 |
| 106 | 2,4-dichlorophenyl | 4-hydroxybutylamino | 141 |
| 107 | 2-chlorophenyl | trans-4-hydroxycyclohexylamino | 176 |
| 108 | 2-chlorophenyl | 3,4-dimethoxybenzylamino | oil |
| 109 | 3-bromophenyl | trans-4-hydroxycyclohexylamino | 88 |
| 110 | 3-bromophenyl | 4-hydroxybutylamino | 129 |
| 111 | 3-bromophenyl | cyclopentylamino | 131 |
| 112 | 3,5-difluorophenyl | trans-4-hydroxycyclohexylamino | 197 |
| 113 | 3,5-difluorophenyl | N-methyl-N-(pyridin-3-ylmethyl)amino | 138 |
| 114 | 3,5-difluorophenyl | 3,4-dimethoxybenzylamino | 131 |

In the column "M.p.", the statement "(mes.)" means that the compound was prepared as methanesulfonic acid salt, and the statement "(HCl)" means that the compound was prepared as hydrochloride. The statement "(dec.)" means that the compound melted with decomposition.

Pharmacological Investigations

Activation of Soluble Guanylate Cyclase

The activation of soluble guanylate cyclase (sGC), which catalyzes the conversion of guanosine triphosphate (GTP) to cyclic guanosine monophosphate (cGMP) and pyrophosphate, by the compounds according to the invention was quantified with the aid of an enzyme immunoassay (EIA) from Amersham. For this, the test substances were first incubated with sGC in microtiter plates and then the quantity of the resulting cGMP was determined.

The sGC employed had been isolated from bovine lung (see Methods in Enzymology, Volume 195, p. 377). The test solutions (100 µl per well) contained 50 mM triethanolamine (TEA) buffer (pH 7.5), 3 mM $MgCl_2$, 3 mM reduced glutathione (GSH), 0.1 mM GTP, 1 mM 3-isobutyl-1-methylxanthine (IBMX), suitably diluted enzyme solution and the test substance or, in the control experiments, solvent. The test substances were dissolved in dimethyl sulfoxide (DMSO) and the solution was diluted with DMSO/water such that the final concentration (c) of test substance in the test batch was 50 µM. The DMSO concentration in the test batch was 5% (v/v). The reaction was started by addition of the sGC. The reaction mix was incubated at 37° C. for 15 to 20 minutes and then stopped by ice-cooling and addition of the stop reagent (50 mM EDTA, pH 8.0). An aliquot of 50 µl was taken and employed for the determination of the cGMP content using the acetylation protocol of the Amersham cGMP EIA kit. The absorption of the samples was measured at 450 nm (reference wavelength 620 nm) in a microtiter plate reading apparatus. The cGMP concentration was determined by means of a calibration curve, which was obtained under the same experimental conditions. The activation of the sGC by a test substance is given as n-fold stimulation of the basal enzyme activity which was found in the control experiments (with solvent instead of test substance), calculated according to the formula:

$$\text{n-fold stimulation} = [cGMp]_{test\ substance}/[cGMP]_{control}.$$

The following results were obtained as shown in Table 2.

TABLE 2

| Compound of Example No. | n-fold stimulation (at c = 50 μM) |
|---|---|
| 26 | 28 |
| 31 | 14 |
| 34 | 22 |
| 35 | 8 |
| 38 | 20 |
| 42 | 23 |
| 53 | 12 |
| 54 | 20 |
| 59 | 17 |
| 68 | 18 |
| 85 | 27 |
| 90 | 14 |
| 97 | 36 |
| 99 | 22 |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claim are to be embraced within their scope.

We claim:

1. A compound of formula I:

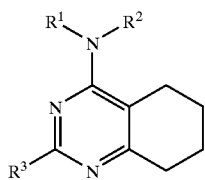

wherein $R^1$ and $R^2$, which are selected independently of one another and which may be identical or different, are hydrogen, or are $(C_1-C_{10})$-alkyl optionally substituted by one or more identical or different substituents selected from hydroxy, $(C_1-C_4)$-alkoxy, $(C_1-C_4)$-alkyl-$S(O)_m$—, $(C_3-C_7)$-cycloalkyl, phenyl, naphthyl, and pyridyl, or are $(C_3-C_9)$-cycloalkyl which can be substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-$SO_2$—NH—, and phenyl-$SO_2$—NH—, or are a residue of a 5-membered to 7-membered saturated heterocyclic ring which contains one or two identical or different heteroatom ring members selected from O, $NR^{10}$, and $S(O)_m$ and is optionally substituted by one or more identical or different substituents selected from $(C_1-C_4)$-alkyl, hydroxy, and aryl-$(C_1-C_4)$-alkyl-, with the exception that $R^1$ and $R^2$ cannot simultaneously be hydrogen, or the residue $R^1R^2N$— is a residue of a 5-membered to 7-membered saturated heterocyclic ring bonded via a ring nitrogen atom which in addition to the nitrogen atom bonded to the tetrahydroquinazoline ring can contain one further heteroatom ring member selected from O and $S(O)_m$, optionally substituted by one or more identical or different substituents selected from $(C_1-C_4)$-alkyl, phenyl, hydroxy, $(C_1-C_4)$-alkoxy, hydroxy-$(C_1-C_4)$-alkyl-, and $R^{11}R^{12}N$—, wherein phenyl groups, naphthyl groups, pyridyl groups, and benzyl groups present in $R^1$, $R^2$, and $R^1R^2N$— can be unsubstituted or substituted on the aromatic ring by one or more identical or different substituents selected from halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, —N($(C_1-C_4)$-alkyl)$_2$, —NH—CHO, —NH—CO—$(C_1-C_4)$-alkyl, CN, —CO—$NH_2$, —CO—NH—$(C_1-C_4)$-alkyl, —CO—N($(C_1-C_4)$-alkyl)$_2$, —CO—OH, —CO—O—$(C_1-C_4)$-alkyl, —CHO, and —CO—$(C_1-C_4)$-alkyl;

$R^3$ is aryl, but cannot be unsubstituted phenyl;

$R^{10}$ is hydrogen, $(C_1-C_4)$-alkyl, aryl-$(C_1-C_4)$-alkyl-, hydroxy-$(C_1-C_4)$-alkyl-, hydroxycarbonyl-$(C_1-C_4)$-alkyl-, (($(C_1-C_4)$-alkoxycarbonyl)-$(C_1-C_4)$-alkyl-, $R^{11}R^{12}N$—CO—$(C_1-C_4)$-alkyl-, $R^{13}$—$SO_2$—, or aryl;

$R^{11}$ and $R^{12}$ are identical or different residues selected from hydrogen and $(C_1-C_4)$-alkyl;

$R^{13}$ is $(C_1-C_4)$-alkyl, aryl, or $R^{11}R^{12}N$—;

aryl is phenyl, naphthyl, or heteroaryl which are optionally substituted by one or more identical or different substituents selected from halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, —N($(C_1-C_4)$-alkyl)$_2$, —NH—CHO, —NH—CO—$(C_1-C_4)$-alkyl, CN, —CO—$NH_2$, —CO—NH—$(C_1-C_4)$-alkyl, —CO—N($(C_1-C_4)$-alkyl)$_2$, —CO—OH, —CO—O—$(C_1-C_4)$-alkyl, —CHO, and —CO—$(C_1-C_4)$-alkyl;

heteroaryl is a residue of a monocyclic 5-membered or 6-membered aromatic heterocycle or of a bicyclic 8-membered to 10-membered aromatic heterocycle, each of which containing one or more identical or different ring heteroatoms selected from N, O, and S; and m is 0, 1, or 2, in any stereoisomeric form, or mixtures thereof in any ratio, or their physiologically acceptable salts.

2. A compound of formula I as claimed in claim 1, wherein one of the residues $R^1$ and $R^2$ is $(C_1-C_8)$-alkyl optionally substituted by one or more identical or different substituents selected from hydroxy, $(C_1-C_4)$-alkoxy, $(C_1-C_4)$-alkyl-$S(O)_m$—, $(C_3-C_7)$-cycloalkyl, phenyl, and naphthyl, or is $(C_3-C_9)$-cycloalkyl which can be substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-$SO_2$—NH—, and phenyl-$SO_2$—NH—, and the other of the residues $R^1$ and $R^2$ is hydrogen, or is $(C_1-C_8)$-alkyl optionally substituted by one or more identical or different substituents selected from hydroxy, $(C_1-C_4)$-alkoxy, $(C_1-C_4)$-alkyl-$S(O)_m$—, $(C_3-C_7)$-cycloalkyl, phenyl, and naphthyl, or is $(C_3-C_9)$-cycloalkyl optionally substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—

O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, wherein phenyl groups, naphthyl groups and benzyl groups present in $R^1$ and $R^2$ can be unsubstituted or substituted on the aromatic ring, or $R^1R^2N$— is a residue of a 5-membered, 6-membered, or 7-membered saturated heterocyclic ring bonded via a ring nitrogen atom which, in addition to the nitrogen atom bonded to the tetrahydroquinazoline ring, may optionally contain one oxygen atom or one group $S(O)_m$ as a further heteroatom ring member and is optionally substituted by one or more identical or different substituents selected from $(C_1-C_4)$-alkyl, hydroxy, $(C_1-C_4)$-alkoxy, hydroxy-$(C_1-C_4)$-alkyl-, and $R^{11}R^{12}N$—, in any stereoisomeric form, or mixtures thereof in any ratio, or their physiologically acceptable salts.

3. A compound of formula I as claimed in claim 1, wherein one of the residues $R^1$ and $R^2$ is $(C_1-C_4)$-alkyl, optionally substituted by one or more identical or different substituents selected from hydroxy, $(C_1-C_4)$-alkoxy, $(C_1-C_4)$-alkyl-$S(O)_m$—, $(C_3-C_7)$-cycloalkyl, phenyl and naphthyl, or is $(C_3-C_9)$-cycloalkyl which can be substituted by one or more identical or different substituents from the group consisting of $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, and the other of the residues $R^1$ and $R^2$ is hydrogen or is $(C_1-C_4)$-alkyl, optionally substituted by one or more identical or different substituents selected from hydroxy, $(C_1-C_4)$-alkoxy, $(C_1-C_4)$-alkyl-$S(O)_m$—, $(C_3-C_7)$-cycloalkyl, phenyl, and naphthyl, wherein phenyl groups, naphthyl groups, and benzyl groups present in $R^1$ and $R^2$ can be unsubstituted or substituted on the aromatic ring, in any stereoisomeric form, or mixtures thereof in any ratio, or their physiologically acceptable salts.

4. A compound of formula I as claimed in claim 1, wherein one of the residues $R^1$ and $R^2$ is $(C_3-C_9)$-cycloalkyl, optionally substituted by one or more identical or different substituents selected from $(C_1-C_4)$-alkyl, benzyl, hydroxy, amino, H—CO—O—, $(C_1-C_4)$-alkyl-CO—O—, $(C_1-C_4)$-alkyl-O—CO—O—, H—CO—NH—, $(C_1-C_4)$-alkyl-CO—NH—, $(C_1-C_4)$-alkyl-O—CO—NH—, phenyl-CO—NH—, $(C_1-C_4)$-alkyl-SO$_2$—NH—, and phenyl-SO$_2$—NH—, phenyl groups and benzyl groups present in $R^1$ and $R^2$ may be unsubstituted or substituted on the aromatic ring, and the other of the residues $R^1$ and $R^2$ is hydrogen, in any stereoisomeric form, or mixtures thereof in any ratio, or their physiologically acceptable salts.

5. A compound of formula I as claimed in claim 1, wherein $R^3$ is substituted phenyl, in any stereoisomeric form, or mixtures thereof in any ratio, or their physiologically acceptable salts.

6. A process for the preparation of a compound of formula I as claimed in claim 1, comprising activating a 4-hydroxytetrahydroquinazoline of formula IV and reacting it with an amine of formula VI,

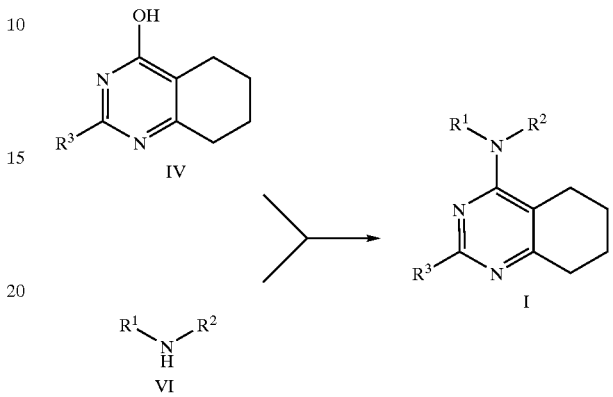

wherein $R^1$, $R^2$, and $R^3$ have the meanings indicated in claim 1.

7. A pharmaceutical composition, comprising at least one compound as claimed in claim 1 and a physiologically acceptable carrier.

8. A method for activating at least one soluble guanylate cyclase, comprising adding at least one compound as claimed in claim 1 to said at least one soluble guanylate cyclase.

9. A method for treating at least one disorder associated with a disturbed cGMP balance, comprising administering an effective amount of at least one compound as claimed in claim 1 to a patient in need thereof.

10. A method for treating hypertension comprising administering an effective amount of at least one compound as claimed in claim 1 to a patient in need thereof.

11. A method for treating stroke comprising administering an effective amount of at least one compound as claimed in claim 1 to a patient in need thereof.

12. A method for treating at least one disorder selected from endothelial dysfunction, diastolic dysfunction, atherosclerosis, thrombosis, restenosis, cardiac insufficiency and pulmonary hypertension, comprising administering an effective amount of at least one compound as claimed in claim 1 to a patient in need thereof.

13. A method for treating at least one disorder selected from angina pectoris and myocardial infarct, comprising administering an effective amount of at least one compound as claimed in claim 1 to a patient in need thereof.

* * * * *

UNITED STATES PATENT AND TRADEMARK OFFICE
CERTIFICATE OF CORRECTION

PATENT NO. : 6,660,746 B1
DATED : December 9, 2003
INVENTOR(S) : Ursula Schindler et al.

It is certified that error appears in the above-identified patent and that said Letters Patent is hereby corrected as shown below:

Title page, Item [54] and Column 1, lines 1-2,
In the title, "4-AMINO-2-ARYL-TETRAHYDOQUINAZOLINES," should read
-- 4-AMINO-2-ARYL-TETRAHYDROQUINAZOLINES, --.

Title page,
Item [57], ABSTRACT,
Lines 13-14, "compounds formula" should read -- compounds of formula --.

Signed and Sealed this

Thirtieth Day of March, 2004

JON W. DUDAS
*Acting Director of the United States Patent and Trademark Office*